US 6,781,688 B2

(12) United States Patent
Kren et al.

(10) Patent No.: US 6,781,688 B2
(45) Date of Patent: Aug. 24, 2004

(54) PROCESS FOR IDENTIFYING DEFECTS IN A SUBSTRATE HAVING NON-UNIFORM SURFACE PROPERTIES

(75) Inventors: George J. Kren, Los Altos Hills, CA (US); Mehdi Vaez-Iravani, Los Gatos, CA (US); David W. Shortt, Milpitas, CA (US)

(73) Assignee: KLA-Tencor Technologies Corporation, San Jose, CA (US)

(*) Notice: Subject to any disclaimer, the term of this patent is extended or adjusted under 35 U.S.C. 154(b) by 0 days.

(21) Appl. No.: 10/327,484

(22) Filed: Dec. 20, 2002

(65) Prior Publication Data

US 2004/0066507 A1 Apr. 8, 2004

Related U.S. Application Data

(60) Provisional application No. 60/415,945, filed on Oct. 2, 2002.

(51) Int. Cl.[7] .............................................. G01N 21/00
(52) U.S. Cl. ............................... 356/237.4; 356/237.2; 356/237.1; 356/394
(58) Field of Search .......................... 356/237.1–237.6, 356/600–601, 392, 394, 398; 250/559.16, 559.18, 559.49; 382/149

(56) References Cited

U.S. PATENT DOCUMENTS

| 5,135,303 | A | * | 8/1992 | Uto et al. ................. 356/237.2 |
| 5,377,001 | A | * | 12/1994 | Malin et al. ............... 356/237.2 |
| 5,416,594 | A | * | 5/1995 | Gross et al. ............... 356/237.5 |
| 5,774,575 | A | * | 6/1998 | Tanaka et al. .............. 382/149 |
| 5,896,294 | A | * | 4/1999 | Chow et al. ................ 700/121 |
| 6,157,444 | A | * | 12/2000 | Tomita et al. ............. 356/237.1 |
| 6,529,270 | B1 | * | 3/2003 | Bills ...................... 356/237.2 |

FOREIGN PATENT DOCUMENTS

| JP | 61259112 | * | 11/1986 | |
| JP | 62289752 | * | 12/1987 | ............. 250/559.49 |

* cited by examiner

*Primary Examiner*—Frank G. Font
*Assistant Examiner*—Sang H. Nguyen
(74) *Attorney, Agent, or Firm*—Beyer Weaver & Thomas, LLP

(57) ABSTRACT

A surface inspection method of the invention includes scanning an inspection surface taking surface measurements. Determinations of various noise levels in the surface are made based on variations in the surface measurements. A dynamic threshold is then determined. The dynamic threshold adapts to the noise levels in the inspection surface to provide a varying threshold that can provide areas of high and low defect sensitivity on the same inspection surface. Defects are then identified by comparing surface measurements with the dynamic threshold. Additionally, the invention includes a surface inspection method that uses signal-to-noise ratios to identify defects. Such a method scans an inspection surface to obtain surface measurements. Noise levels associated with the inspection surface are then determined. Signal-to-noise ratios are determined for the surface measurements. The signal-to-noise ratios are compared with a signal-to-noise ratio threshold value. Defects are identified based on the comparisons of the signal-to-noise ratio of the surface measurements with the signal-to-noise ratio threshold value.

25 Claims, 9 Drawing Sheets

US 6,781,688 B2

PROCESS FOR IDENTIFYING DEFECTS IN A SUBSTRATE HAVING NON-UNIFORM SURFACE PROPERTIES

RELATED APPLICATIONS

This application claims priority to the U.S. Provisional Patent Application Serial No. 60/415,945, entitled "Process For Identifying Defects in a Substrate Having Non-Uniform Surface Properties", filed on Oct. 2, 2002, which is hereby incorporated by reference in its entirety for all purposes.

TECHNICAL FIELD

The invention described herein relates generally to surface inspection and testing. In particular, the invention relates to methods for identification in surfaces and substrates used in semiconductor fabrication and processing.

BACKGROUND

For many years, various brightfield, darkfield, and e-beam scanning methodologies have been used to inspect surfaces. These scanning technologies make use of light scattered and/or reflected by a surface to characterize and examine features of the surface. The details of these and other related scanning and inspection technologies are well known to those having ordinary skill in the art.

In many of these type devices, an inspection surface is secured in an inspection device and then a light beam is projected on the inspection surface. The light beam is then scanned across the portions of the surface that are to be inspected. Appropriately placed detectors detect light from the inspection surface. The detectors generate signals corresponding to the detected light. These signals are then processed using a variety of different methodologies to determine various surface characteristics. Of particular interest are surface features that are referred to as defects. The detection and quantification of defects is important in many areas. In particular, defect detection and analysis are important in semiconductor processing. Defects include, but are not limited to, particles, pits, bumps, scratches, and a number of other features that mar the inspection surface.

Although existing machines and processes accomplish their designed purposes exceptionally well, they have some limitations. Existing machines and processes can detect defects in highly polished regular surfaces very well, but they can have difficulty detecting defects in certain non-uniform surfaces. In one example, currently used detection techniques have difficulties detecting the presence of defects in patterned surfaces. Conventional techniques have difficulties discerning between changes in a surface pattern and the presence of a defect. Such patterned surfaces include, but are not limited to, patterned semiconductor wafer surfaces and patterns formed on masks. Conventional processes are also known to have some difficulties detecting defects in surfaces that have other types of non-uniform surface characteristics. Surfaces having areas of differing surface properties can make defect detection a difficult prospect. For example, an inspection surface having relatively polished regions and also having regions of significantly greater surface roughness can present inspection difficulties. Using conventional inspection processes on such surfaces can result in failures to detect small defects and also the detection of "false positives". False positives are instrument readings that indicate the presence of a defect where no defect actually exists. These false positives are a serious problem for reasons that are discussed in greater detail hereinbelow.

For these and other reasons, improved surface inspection methodologies are needed.

SUMMARY OF THE INVENTION

In accordance with the principles of the present invention, a method of surface inspection is disclosed. Generally, the method scans the inspection surface to obtain surface measurements. Determinations of various noise levels in the surface are made based on variations in the surface measurements. A dynamic threshold is then determined based on the varying noise levels in the surface. The dynamic threshold adapts to the noise levels in the inspection surface to provide a varying threshold that adjusts to areas of high and low surface noise in the same inspection surface. In some embodiments, such a varying threshold involves adjusting the sensitivity of the threshold based on the surface noise levels. Defects are then identified by comparing surface measurements with the dynamic threshold.

In one method embodiment, the surface is scanned to obtain surface measurements. The surface measurements are used to generate a baseline. A dynamic threshold associated with the surface measurements and the baseline is generated. Defects are identified using comparisons of surface measurements with at least one of the baseline and the dynamic threshold.

The embodiments of the invention also include a surface inspection method that uses signal-to-noise ratios to identify defects. Such an embodiment scans an inspection surface to obtain surface measurements. Noise levels associated with the inspection surface are then determined. Signal-to-noise ratios are determined for the surface measurements. The signal-to-noise ratios are compared with a signal-to-noise ratio threshold value. Defects are identified based on the comparisons of the signal-to-noise ratio of the surface measurements with the signal-to-noise ratio threshold value.

These and other aspects of the present invention are described in greater detail in the detailed description of the drawings set forth hereinbelow.

BRIEF DESCRIPTION OF THE DRAWINGS

The following detailed description can be more readily understood in conjunction with the accompanying drawings, in which.

It is to be understood that, in the drawings, like reference numerals designate like structural elements. Also, it is understood that the depictions in the Figures are not necessarily to scale.

DETAILED DESCRIPTION OF THE DRAWINGS

The present invention has been particularly shown and described with respect to certain embodiments and specific features thereof. The embodiments set forth hereinbelow are to be taken as illustrative rather than limiting. It should be readily apparent to those of ordinary skill in the art that various changes and modifications in form and detail may be made without departing from the spirit and scope of the invention.

Figure 1:
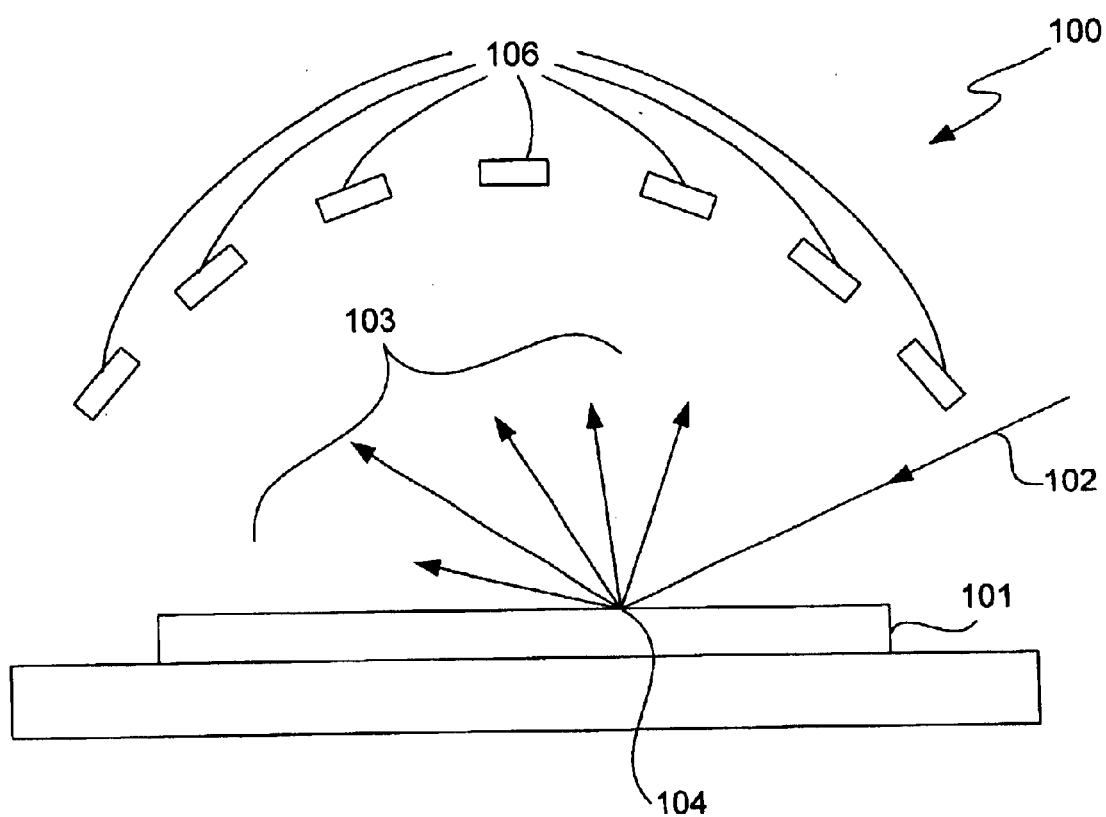
FIG. 1 is a simplified schematic cross-sectional view of an example of a darkfield surface inspection tool.

The following detailed description describes various embodiments of inspection methods in accordance with the principles of the present invention. FIG. 1 is a simplified schematic cross-section view of an inspection tool 100 having an inspection surface 101 positioned therein. The present invention can be used to detect defects using a wide array of inspection devices known to persons having ordinary skill in the art. Typical examples include, but are not limited to, darkfield, brightfield, and e-beam surface inspection tools and techniques. Additionally, the principles of the invention can be applied to acoustic microscopy and probe microscopy. In fact, the disclosed inventive principles can be advantageously applied to any technique for detecting anomalies in the presence of background noise. Examples of specific tools that can be suitably employed in conjunction with teachings herein include, without limitation, the Surfscan SP 1 DLS Surface Inspection System, the AIT-XP Surface Inspection System, and eS20XP Surface Inspection System all manufactured by KLA-Tencor Technologies Corporation of San Jose, Calif. As is known to those having ordinary skill in the art, the principles of the invention taught herein can be applied to a wide range of other surface inspection tools.

FIG. 1 schematically depicts one simplified example of a typical inspection tool 100 (e.g., a darkfield inspection tool). An inspection surface 101 is positioned in the tool 100 and the surface 101 is illuminated by a light beam 102. Portions of the light beam 102 are scattered from the inspection surface as beams 103. The beams 103 are detected by the photodetectors 106 and used to provide surface measurements that correspond to the point 104 being inspected. Commonly, the inspection surface 101 is scanned by illuminating specific portions of the surface and taking corresponding measurements of the resultant beams 103. As is known to persons of ordinary skill in the art, many different photodetectors 106 and photodetector arrangements can be used to make such measurements. Additionally, a variety of light shaping elements (e.g., lenses, reflectors, collimators, filters, and many other types of optical elements) can also be used in conjunction with the photodetectors to enhance the properties of the inspection tools.

In order to locate defects in an inspection surface, a variety of points on the surface are scanned. Surface measurements are typically obtained for each scanned point of the inspection surface.

Figure 2:
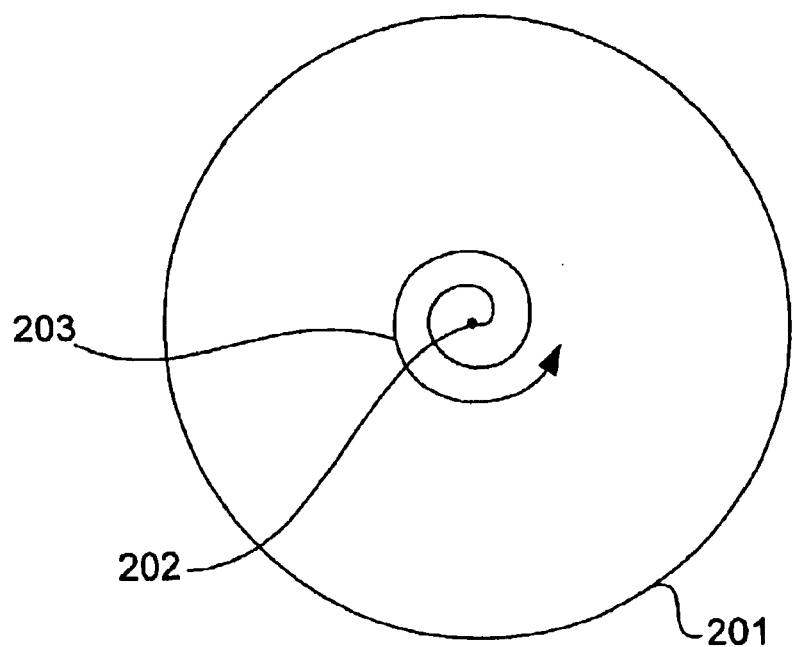
FIG. 2 is a plan view of an inspection surface showing one type of scanning pattern that can be used for surface inspection in accordance with the principles of the present invention.

FIG. 2 diagrammatically depicts one common scanning pattern used for surface inspection. An inspection surface 201 (here, a semiconductor wafer) is placed in an inspection tool and then a light beam is scanned across the desired portions of the inspection surface. Typically, the light beam is generated by a laser which forms a focused light spot 202 on the inspection surface 201. Common spot 202 sizes range from about 20 μm (micron) in diameter to larger diameters. The spot is scanned across the surface. This is commonly accomplished by moving the inspection surface relative to the light beam. In one implementation, the inspection surface 201 is rotated and translated such that the spot 202 moves in a spiral pattern 203 (as depicted schematically by the spiral arrow) across the inspection surface 201. Light scattered from the spot is detected by the photodetectors of the inspection tool. The photodetectors generate electronic signals corresponding to the light received for each point on the inspection surface. These electronic signals are also referred to as surface measurements. Surface measurements are made for each point along the spiral pattern. Each measurement corresponds to a different point on the inspection surface 201. In this way, if desired, the entire surface can be scanned.

Figure 3:
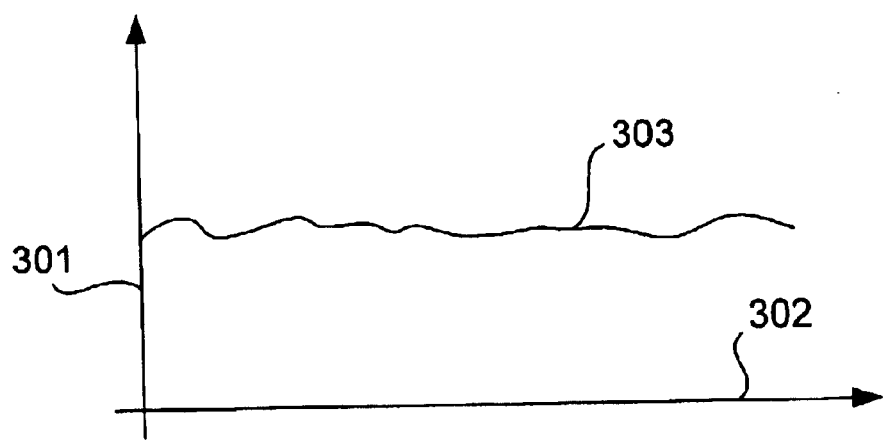
FIG. 3 is a graphical depiction of a plot of measurement signal intensity versus measurement position or time.

The electronic signals from the photodetector can be mapped in a variety of ways known to those having ordinary skill in the art. In one example, signal intensity can be mapped on one axis and time can be mapped along another axis. Because the rotational pattern and rotational velocity of the scanning process are known, time can be related to position on the inspection surface. In such a mapping, the relationship between signal intensity and position on the inspection surface can be determined. One simplified example of such a mapping is depicted in FIG. 3. Signal intensity is mapped on a first axis 301 and time is mapped on a second axis 302. In this depiction, the signal 303 is depicted as a continuously modulating line with each of the individual data points for each surface measurement connected by a single line. Other graphical depictions and mappings may be used.

Figure 4A:
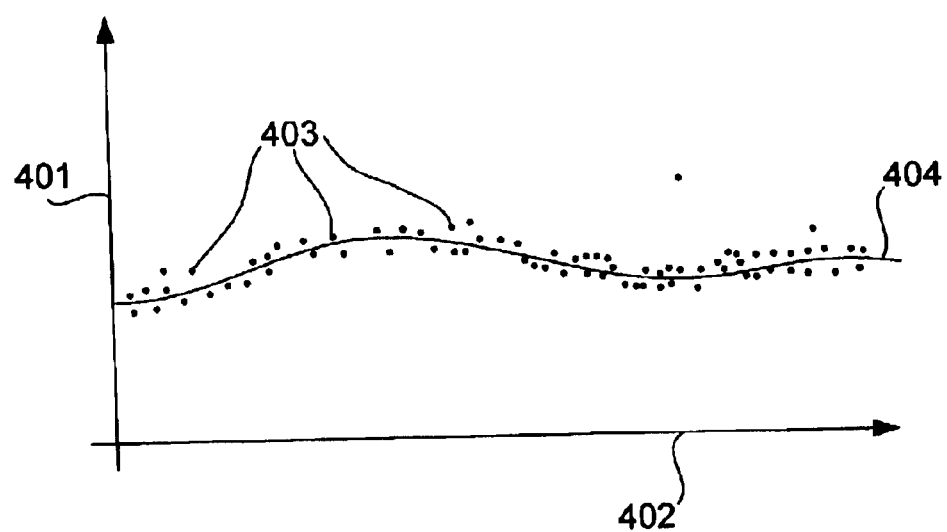
FIGS. 4(a) and 4(b) are depictions of conventional haze maps for a relatively uniform inspection surface. Included are depictions of a baseline and a conventional defect threshold.

FIG. 4(a) depicts another mapping of surface measurements obtained during a scanning of an inspection surface. Such a depiction is referred to herein as a "haze map". The individual dots 403 each correspond to surface measurements. The pattern of dots is an electronic representation of surface characteristics of the inspection surface mapped using signal intensity 401 and (in this depiction) time 402. Using the pattern of dots (surface measurements), a baseline curve or baseline 404 can also be generated. The baseline 404 is a smoothed line that can be used to generally describe aspects of the inspection surface. Such a baseline 404 can be obtained by filtering the surface measurements using a variety of methods known to persons having ordinary skill in the art. In one implementation, low-pass filtering can be used. Thus, surface measurements having extremely high signal intensity values can be excised from calculations of a baseline 404. In the depicted embodiment, the baseline 404 is defined by filtering the surface measurements such that a moving median of the values of the surface measurements is generated. For example, the moving median can be obtained by taking the median value for 100 surface measurements. The number of measurements used and methods for determining such baselines 404 encompasses a wide range of signal processing options known to those having ordinary skill in the art. For example, in one alternative approach, filtering can be used to generate a moving average of the surface measurements. In other filtering implementations, where signal processing capacity is limited and quick response times are desired, surface measurements having signal intensity values in the uppermost regime and in the lowermost regime can be discarded and the remaining surface measurements can be used to generate the baseline 404. For example, surface measurements having signal intensity values in the uppermost 25% of value are discarded and surface measurements having signal intensity values in the lowermost 25% of value are discarded. A moving median of the remaining 50% of surface measurements can be used to generate the baseline 404. Of course, the foregoing is merely an illustrative example, the inventors contemplate the use of many other filtering methods or data smoothing implementations to generate suitable baselines 404 in accordance with the principles of the present invention.

Figure 4B:
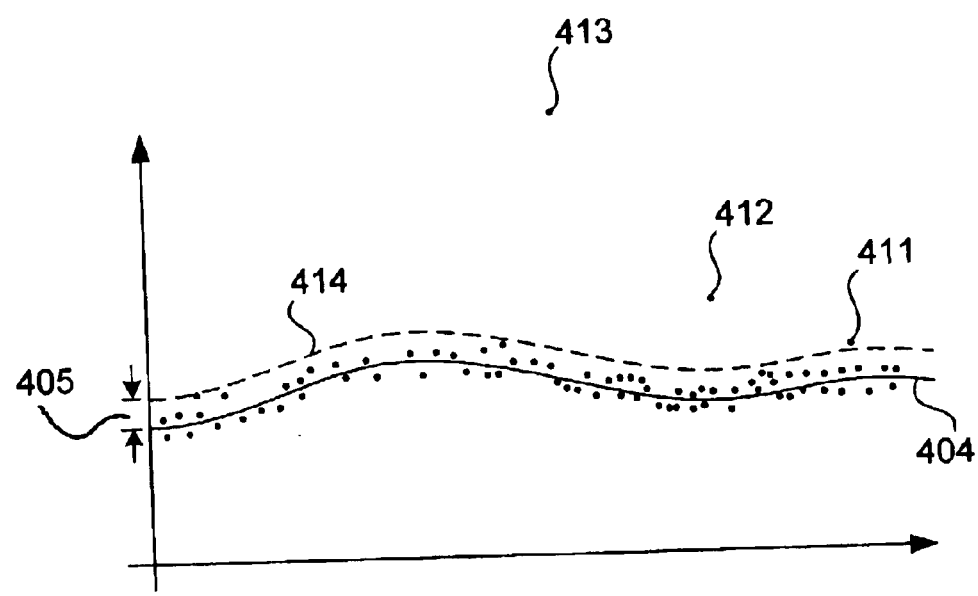

The haze maps of FIGS. 4(*a*) and 4(*b*) correspond to a relatively uniform inspection surface. Consequently, signal intensities of the surface measurements will fall in the same general range as the baseline 404 without a great degree of variation. In a conventional approach, a threshold tolerance value 405 is then chosen for the haze map. The threshold tolerance value 405 is set relative to the baseline 404. Commonly, the threshold tolerance value 405 is constant and applies for the entire inspection surface. The threshold tolerance value 405 defines a defect threshold 414 (the dashed line) which can be used to help identify defects in the inspection surface. Surface measurements that have signal intensities greater than the limit defined by the defect threshold 414 are identified as defects. Referring to the haze map of FIG. 4(*b*), surface measurements corresponding to points 411, 412, and 413 exceed the defect threshold 414 and are thus defined as defects.

The conventional methods depicted in FIGS. 4(*a*) and 4(*b*) can detect defects very well under certain proscribed conditions. However, such methodologies have certain limitations. For example, defects become difficult to detect when non-uniform or patterned surfaces are inspected. In another limitation, these existing methodologies are not intended to detect surface noise caused by variations in the inspection surface nor are they intended to detect signal to noise ratios in the surface measurements.

Another significant limitation in conventional approaches, mentioned briefly hereinabove, is the generation of "false positive" defect readings. If too many defects are reported, assembly lines and process machines must be stopped and readjusted until the cause of the defects is ascertained and eliminated. The costs involved in such stopping and restarting of the affected assembly lines are substantial. In some cases, these costs can run into the millions of dollars. Thus, it is very important that the diagnosis of defects be made with a high degree of confidence. Referring again to FIGS. 4(*a*) and 4(*b*), it can be seen that surface measurements 413 and even 412 are probably defects. However, a level of uncertainty exists with respect to surface measurement 411, which just barely exceeds the defect threshold 414. A method that can help resolve these more uncertain defect identifications with a higher degree of confidence is desirable.

These problems of certitude in defect identification become magnified when the inspection surface itself includes various regions of differing surface characteristics. Examples of such surface characteristics include, but are not limited to, variations in surface roughness, variations in surface color, variations in surface reflectivity, variations in films formed on the surface, the presence of patterns in the surface, pattern variation in the surface, and other variations in surface properties. In such varying surface conditions, thresholds set to detect surface defects under one set of surface conditions may not be useful for detecting defects in other regions of a surface having a differing surface.

Figure 5A:
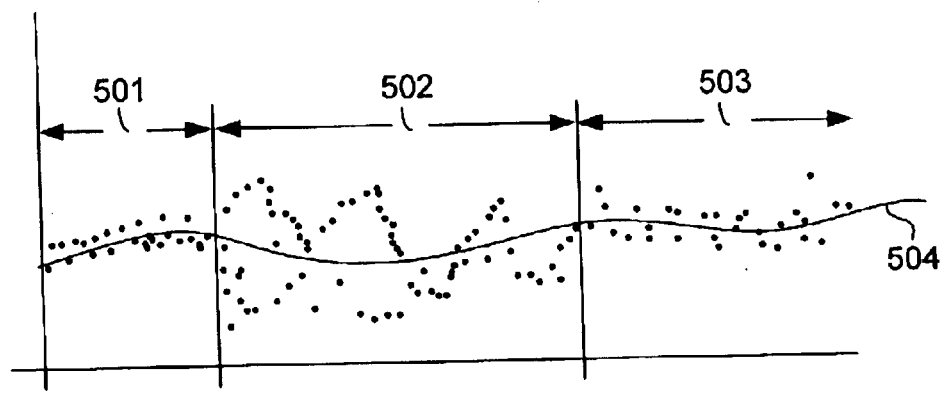
FIGS. 5(a)–5(c) are depictions of conventional haze maps for an inspection surface with regions of significantly differing surface characteristics. A baseline and different conventional defect thresholds are also depicted.
Figure 5B:
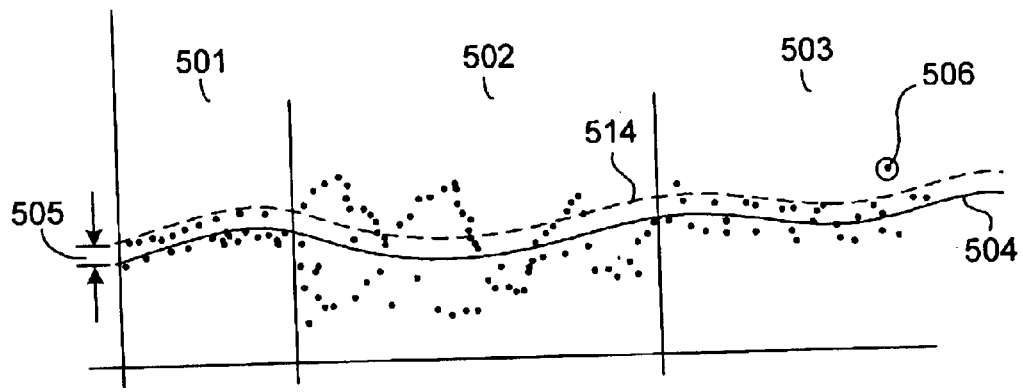

FIGS. 5(*a*)–5(*c*) schematically depict mappings of an inspection surface having more variation in its surface properties. FIG. 5(*a*) depicts an inspection surface having regions of varying surface characteristics. The surface measurements (the dots) are mapped to generate a haze map and processed to generate a baseline 504. The depicted haze map includes a first domain 501 where the surface measurements demonstrate little variation from the baseline 504. This can indicate that the portion of the inspection surface corresponding to the first domain 501 has relatively uniform surface properties and is a relatively smooth surface. As a result, there is relatively little surface noise generated in the first domain 501. The concept of surface noise (also referred to herein as "noise") will be explained in greater detail hereinbelow.

FIG. 5(*a*) also depicts a second domain 502 wherein the surface measurements demonstrate a greater degree of variation from the baseline 504 than the more uniform regions of the inspection surface. As indicated earlier, this increased variation of the surface measurements from the baseline 504 can be caused by a variety of surface conditions including, but not limited to, variations in surface roughness, variations in surface color, variations in surface reflectivity, variations in surface film thickness, color, and transparency, surface pattern variation, as well as other variations in surface properties. In one example, the first domain 501 can be a highly polished region of the inspection surface having relatively little surface roughness. In contrast, the second domain 502 can be a region of increased surface roughness. Finally, the third domain 503 is depicted as a relatively smooth surface having surface measurements in the same general range as the baseline 504 without a large degree of variation.

FIG. 5(*b*) depicts one conventional approach for identifying defects. In such an approach, a threshold tolerance value 505 is determined and maintained at a constant level. This threshold tolerance value 505 is used in conjunction with a baseline 504 to define a defect threshold 514 for identifying defects. As shown, the defect threshold 514 effectively identifies some defects in the first domain 501 and the third domain 503. For example, the surface measurement 506 (inside the circle) can be readily identified as a defect. However, due to the increasing noise levels in the second domain 502, the same defect threshold 514 cannot reliably detect defects in the second domain 502. Using the defect threshold 514, all values in excess of the defect threshold 514 will be reported as defects in the inspection surface. Such a situation results in a high number of normal (non-defect) variations in surface measurements being reported as "defects". For this reason, setting the threshold tolerance value 505 at a level designed to locate defects in a smooth surface is not very useful for detecting defects in rougher regions (or regions having other different surface characteristics) of the surface. Such existing methodologies are unable to sort out defects from routine local changes in surface characteristics. Again, this leads to a large number of reported false positives.

Figure 5C:
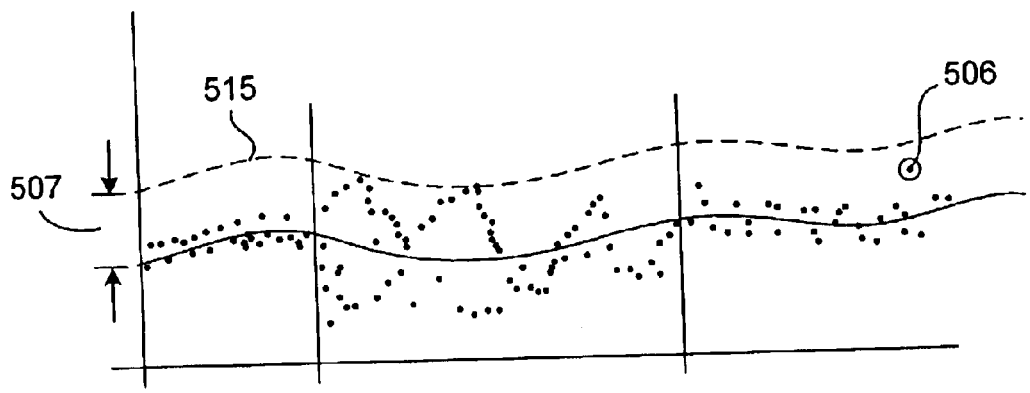

FIG. 5(c) depicts an approach that conventional methodologies use to reduce the number of false positives caused by noisier surface conditions. Existing methodologies change the threshold tolerance value for the defect threshold. In the depicted example, a new threshold tolerance value 507 having a higher value is used to raise the defect threshold 515. One of the drawbacks of this approach is that it reduces the overall sensitivity of the system. This means that, although the incidence of false positives is reduced, it is also possible to miss "real" defects due to the decreased sensitivity of the system. As depicted in the example of FIG. 5(c), a higher defect threshold 515 misses the defect associated with surface measurement 506.

What is needed is a method that can reliably detect defects in inspection surfaces having relatively "quiet" surface domains (e.g., domains 501 and 503) and having noisier surface domains 502. Additionally, such a method should also reduce the reporting of false positives in the surface domains (e.g., domain 502) where the surface measurements demonstrate greater variation. An advantage of such an invention is that it can detect defects over a wide range of varying surface conditions in one inspection pass. One particularly advantageous feature of the invention is the ability to detect defects in patterned surfaces. Such an invention is particularly valuable when applied to defect detection patterned semiconductor wafer surfaces and lithography pattern masks. In such patterned surfaces, there can be regions of highly polished surfaces patterned to include deep "well" regions having very high aspect ratios. The present invention can detect defects in such surfaces.

Figure 6A:
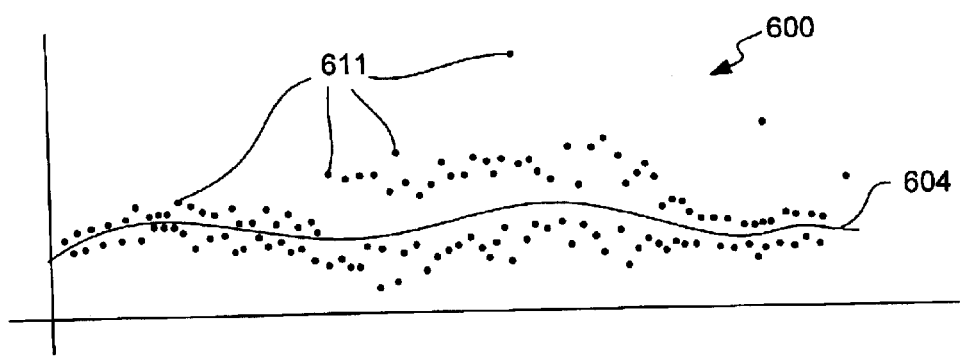
FIGS. 6(a)–6(d) depict an inspection surface having regions of significantly differing surface characteristics. The figures show a baseline and conventional defect thresholds compared with a dynamic threshold embodiment in accordance with the principles of the present invention.

FIGS. 6(a)–6(d) are depictions of the same inspection surface illustrating some aspects of the present invention. FIG. 6(a) depicts a mapping of a plurality of surface measurements 611 (the dots) obtained from an inspection surface. The plurality of surface measurements 611 are used to generate a haze map 600 and an associated baseline 604.

Figure 6B:
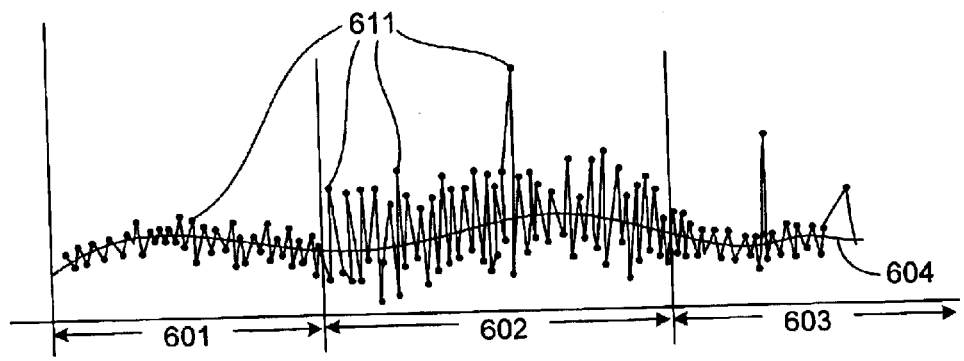

The view presented in FIG. 6(b) can be used to more readily explain certain aspects of the present invention. Each of the surface measurements 611 is depicted as connected by a single contiguous line. As can be seen, there is considerable variation in the signal intensity. Although the variations in signal intensity can have many causes, in this example, the noise variation is caused by variations in surface roughness. For example, the first domain 601 and the third domain 603 are regions of relative smoothness. In contrast, the second domain 602 is a region of relatively rougher surface characteristics. This results in the second domain 602 having measurements with greater variation from the baseline 604. It should be noted that the sensitivity of most of the inspection tools is such that a series of haze maps taken of the same inspection surface will generate very nearly identical haze maps. The point being that variation in signal intensity is due to variations in surface characteristics rather than errors in the instrumentation. Thus, the haze map can be used to provide an accurate map of the surface characteristics (e.g., topology) for the inspection surface.

Figure 6C:
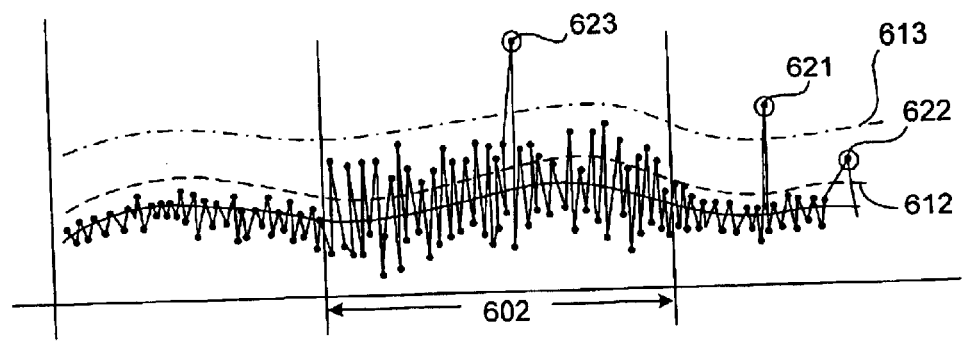

FIG. 6(c) depicts a first defect threshold 612 (the dashed line). The first defect threshold 612 is used in conventional defect identification techniques. In such conventional methodologies, all surface measurements in excess of the first defect threshold 612 are identified as defects. As applied here, two defects (621, 622) are identified in the third domain 603. Another defect 623 is identified in the second domain 602. Unfortunately, in this conventional process, the first defect threshold 612 leads to the identification of a large number of other surface measurements in the second domain 602 as defects (i.e., false positives). Moreover, using existing methodologies, defect 623 cannot be discerned from the other surface measurements that exceed the first defect threshold 612. Thus, true defects cannot be distinguished from false positives. Instead, all surface measurements that exceed the first defect threshold 611 are identified as defects. Some existing methodologies raise the defect threshold to compensate for increasing surface variation. An example of this approach is also depicted in FIG. 6(c). A higher second defect threshold 613 (depicted by the dotted and dashed line) is depicted. As can be seen, the false positives (as well as any actual small defects) in the second domain 602 no longer read as defects. The defects 621 and 623 are still identified as defects. The problem is that such existing methods will now miss defect 622.

In one embodiment of the present invention, this problem is addressed by generating an adaptive defect threshold in a process referred to herein as "dynamic thresholding". Dynamic thresholding adjusts the level of the defect threshold based on the degree of variation of the surface measurements from the baseline. Thus, in areas of the inspection surface where the degree of variation in the surface measurements is high (i.e., noisy regions), the defect threshold is adapted to reflect this increased variation from the baseline. Also, where the degree of variation in the surface measurements is smaller (less noisy regions), the threshold can be lowered to increase sensitivity and thereby be more sensitive to smaller, less apparent, defects which would be lost if the threshold used in the "noisier" regions was used.

Figure 6D:
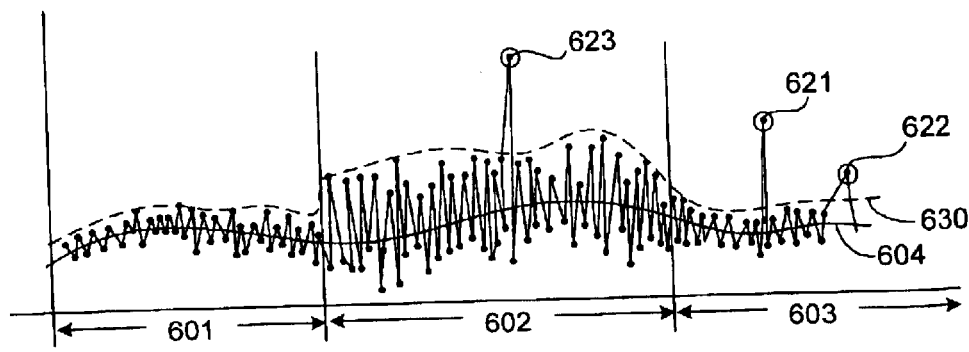

FIG. 6(d) graphically depicts one embodiment of the invention using dynamic thresholding to adapt the defect threshold to trends in surface characteristics to generate a varying threshold value that adapts to changing surface conditions. Such dynamic thresholding generates (in this case) a time varying dynamic threshold 630 (depicted with the dashed lines) that is responsive to changing surface conditions. The dynamic threshold 630 adapts to the surface measurements such that regions of the surface having lower noise characteristics define regimes of higher sensitivity (lower defect thresholds). Conversely, regions of the surface having greater noise characteristics define regimes of lower sensitivity (higher defect thresholds). In the depicted embodiment, the first domain 601 is a region where the surface measurements do not vary much from the baseline 604. In this example, one such domain is a surface region polished to a high degree of smoothness. As a result, the dynamic threshold 630 in such domains is relatively small. A reduced dynamic threshold is more sensitive to variations in surface measurements and is therefore more sensitive to defects.

The second domain 602 is a region where the surface measurements have an overall increased variance from the baseline 604. A typical example is a surface region having relatively rougher surface characteristics. Thus, the portion of the dynamic threshold 630 in the second domain 602 defines a regime of less sensitivity. This is reflected by higher threshold values which are less sensitive to surface measurement variation from the baseline 604. As a result, such a threshold is less likely to result in the generation of false positive readings. The third domain 603 is another region of relative quietude. As a result, the dynamic threshold 630 in such domains is relatively smaller. Such smaller threshold values are more sensitive to variations in surface measurements and are therefore relatively sensitive to defects. A result of such dynamic thresholding is that the actual defects can still be identified (e.g., 621, 622, and 623) while the reporting of false positive readings is significantly reduced.

The dynamic threshold can be determined as surface measurements are being taken ("on the fly") or as part of a subsequent surface analysis conducted after the surface measurements have been taken and the inspection has been completed.

Figure 7:
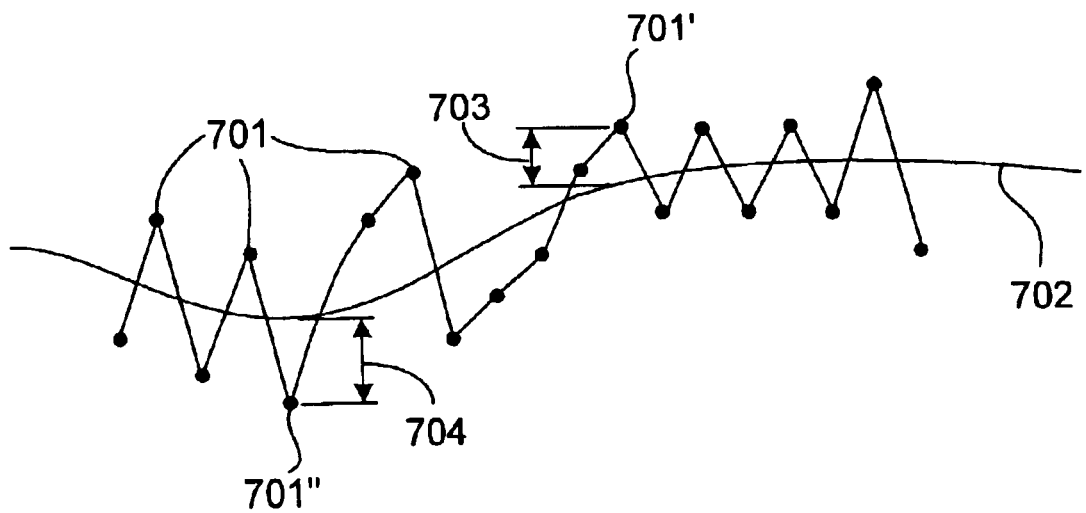
FIG. 7 is a close-up view of a portion of a haze map embodiment showing baseline and signal amplitude embodiments in accordance with the principles of the present invention.

FIG. 7(*a*) illustrates some of the concepts used in one embodiment of accomplishing dynamic thresholding. A number of surface measurements (e.g., represented by the dots 701) are taken and mapped. A baseline 702 (the dashed line) can be calculated using a variety of smoothing, filtering, or other signal processing methods known to those having ordinary skill in the art. Once the baseline 702 is generated, signal amplitudes are determined for the surface measurements. As used herein, signal amplitudes are defined as the distance a surface measurement lies above or below the baseline 702. These signal amplitudes can be thought of as the variation of the surface measurements 701 from the baseline 702 due to variations in the surface characteristics of the inspection surface. For example, the signal amplitude associated with surface measurement 701' is shown as the distance 703 between the local baseline value 702 and the surface measurement 701'. In another example, the signal amplitude associated with surface measurement 701" is shown as the distance 704 between the local baseline value 702 and the surface measurement 701". These signal amplitudes can be used to define a dynamic threshold for each inspection surface.

In one approach, raw data obtained by scanning an inspection surface is stored in a memory. Statistical analysis is then performed on the stored data to provide relevant statistical information (e.g., localized variance of the raw data, etc.). As is known to persons having ordinary skill in the art, many other types of useful statistical information can be generated in this fashion and detailed explanations will not be provided here. This statistical information can be used to set appropriate local thresholds for defect detection (which adapt in response to changes in the localized characteristics of the surface). The raw data can also be used in a moving average procedure (such as known to those having ordinary skill in the art). Such a procedure can provide useful information and analysis used to generate base-line values for subsequent data analysis. In general, dynamic thresholding identifies surface regions of the inspection surface having greater and lower levels of surface noise. Then, in accordance with threshold tolerance criteria identified by process engineers or using specialized algorithms, a dynamic threshold is determined for the inspection surface. Then defects are identified.

Referring back to FIGS. 6(*a*)–6(*b*), such a surface can be characterized by dynamic thresholding. Surface measurements are taken and a baseline (e.g., baseline 604) can be generated. Signal amplitudes are then determined for the surface measurements. A noise value or noise curve for these signal amplitudes can then be generated. Such a noise curve can be used to characterize the noise levels in an inspection surface. Regions of relatively greater and lesser noise can be located and quantified. Many methods for so characterizing surfaces are known to those having ordinary skill in the art of statistical signal processing. In one example, the signal amplitudes used in the noise curve can be filtered, smoothed, or otherwise processed to generate noise curves less affected by extreme surface measurements (e.g., defects). In one such implementation, root mean squared values for the signal amplitudes can be used to generate a noise curve. Then, for example, a value defined by one or two standard deviations can be used to set a threshold tolerance value that can be used, in conjunction with the baseline to generate a dynamic threshold for the inspection surface. These and a great variety of other signal processing approaches known to persons having ordinary skill in the art can be used to generate such dynamic thresholds.

Using such a noise curve to generate a dynamic threshold is only one implementation of the principles of the present invention. Alternatively, a noise curve can be used as a noise baseline for comparison with individual surface measurements to generate signal-to-noise ratios associated with each surface measurement. One tremendous advantage of such an approach is that the signal-to-noise ratios, alone, can be used to determine the presence of defects regardless of the variations in surface noise levels. Still more advantageously, the signal-to-noise ratio can be used to quantify the certainty of such defect identification. This means that signal-to-noise ratio can be used to find defects in surfaces having widely varying surface characteristics. This also means that signal-to-noise ratio can be used to permit the diagnosis of defects with a higher degree of confidence that the defect identification is correct (i.e., reduce the incidence of false positives). The following Figures help illustrate some of these concepts.

The embodiments described with respect to FIGS. 8(*a*) and 8(*b*) and FIGS. 9(*a*)–9(*c*) illustrate a defect detection approach utilizing a signal-to-noise ratio approach. When an inspection surface having varied surface characteristics is scanned by an inspection tool in accordance with the principles of the present invention, a graphical depiction such as that of FIG. 8(*a*) can be obtained. In one implementation, a darkfield inspection tool can be used to obtain surface measurements. A plurality of such surface measurements 801 are mapped onto a two axis coordinate plane generating a haze map 800 of the inspected surface. For example, signal intensity can represent one axis and time (or position) another axis. In the depicted embodiment, a corresponding baseline 802 is also depicted. As can be seen, the inspection surface has considerable variation in its surface characteristics. The majority of the surface is relatively quiescent. However, the depicted surface includes two regions (803, 804) where the surface measurements have increased variance from the baseline 802 (i.e., noisy surface regions) which can be indicative of rougher surface characteristics. As stated previously, surfaces having greater variation from the baseline can be indicative of a number of other surface conditions (or combinations of surface conditions) including, but not limited to, greater variation in surface roughness, greater variation in surface reflectivity, varying surface film thickness, patterning, as well as other varied surface conditions. All can give rise to increased variance from the baseline 802. FIG. 8(*a*) also includes a circled portion 805 of the haze map 800 that is depicted in expanded view in FIG. 8(*b*).

This variation in the signal amplitudes from the baseline 802 can be used to characterize the inspection surface in heretofore unknown ways. FIG. 8(*b*) shows a baseline 802 and exemplar signal amplitudes 811, 812. These signal amplitudes can also be thought of as measurements of "noise" in the surface and are also referred to as noise amplitudes. Once noise amplitude values are determined (for all or a portion of the inspection surface), they can be subject to signal processing. Such signal processing can include filtering or other processing techniques used to reduce the effects of aberrant or outlying data points.

Once filtered and/or processed, the noise amplitude values can be used to characterize the overall surface noise in the inspection surface. For example, in one embodiment, the noise amplitude values can be filtered using calculated root mean squared (rms) noise values. The rms noise values can be used to produce a map characterizing the noise in an inspection surface. For example, referring to the lower portion of FIG. 8(b), a schematic noise map is depicted. Rms noise values can be used to generate a calculated surface noise curve 806 associated with the surface portion 805. In the depicted embodiment, a noise curve 806 is generated using a moving median value of the rms noise for the surface. As can easily be seen, the right hand side of the calculated surface noise curve 806 is indicative of the relatively higher noise level present in the corresponding portion of the inspection surface. Although rms noise values and a moving median noise value is used here to generate a noise curve 806, many other filtering and quantification techniques known to persons having ordinary skill in the art can be used to define the noise characteristics of the inspection surface.

Figure 8A:
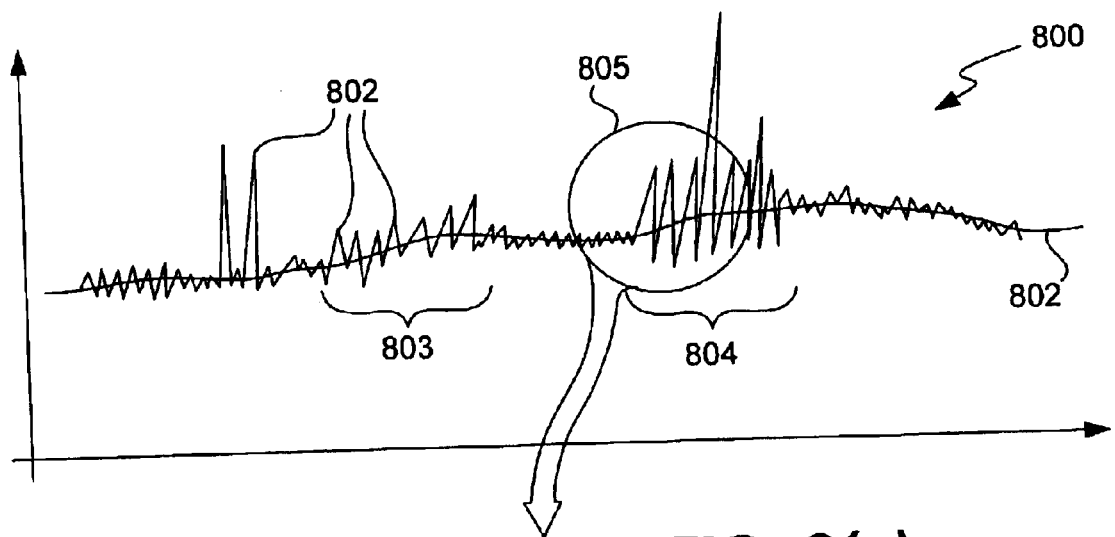
FIG. 8(a) depicts a portion of a haze map for an inspection surface with varying surface characteristics and a baseline generated in accordance with the principles of the present invention.
Figure 8B:
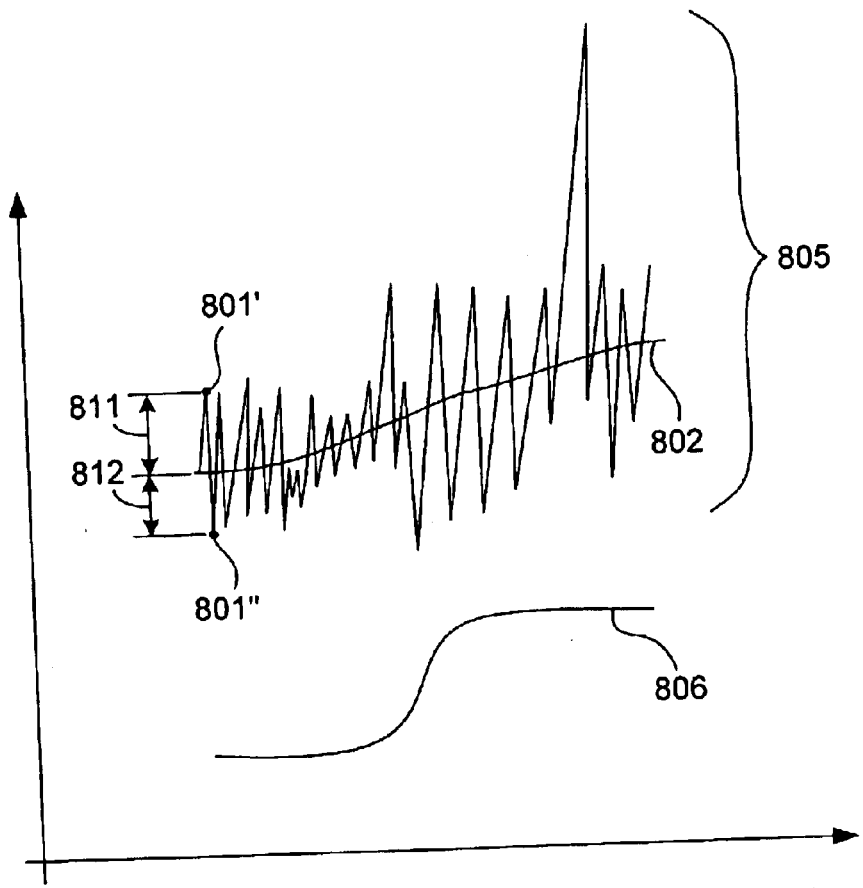
FIG. 8(b) is a close-up view of a portion of the haze map of FIG. 8(a) also depicting a noise curve embodiment generated in accordance with the principles of the present invention.

In some embodiments (such as that depicted in FIGS. 8(a) and 8(b) above), it is advantageous, but not required, to calculate the noise values as positive numbers representing the magnitude of the noise. Additionally, the generation of noise curves is not limited to using a moving median or moving average of the noise values. Many other suitable methods known to those having ordinary skill in the art can be used to generate satisfactory noise curves.

The surface noise curve can be used in conjunction with the signal amplitude information for individual surface measurements to identify defects and determine a confidence level for such defects. One embodiment for achieving this objective uses signal to noise ratio. An implementation of this method embodiment can be more easily illustrated with reference to FIGS. 9(a)–9(c).

Figure 9A:
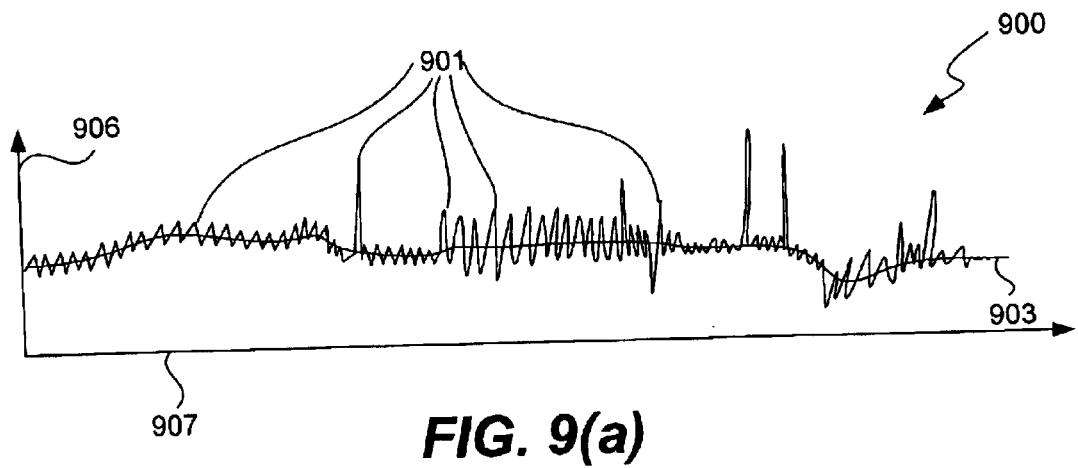
FIGS. 9(a)–9(c) are graphical depictions of an inspection surface shown using a haze map, associated noise map, and associated plot of signal-to-noise ratios in accordance with the principles of the present invention.

FIG. 9(a) is a graphic representation of surface measurements from a portion of an inspection surface measured with an inspection tool (e.g., a darkfield inspection tool or other related inspection tool) in accordance with the principles of the present invention. A first axis 906 represents signal intensity and a second axis 907 represents time (or position). A plurality of surface measurements 901 are mapped onto a haze map 900 that includes a baseline 902 associated with the surface measurements 901.

Figure 9B:
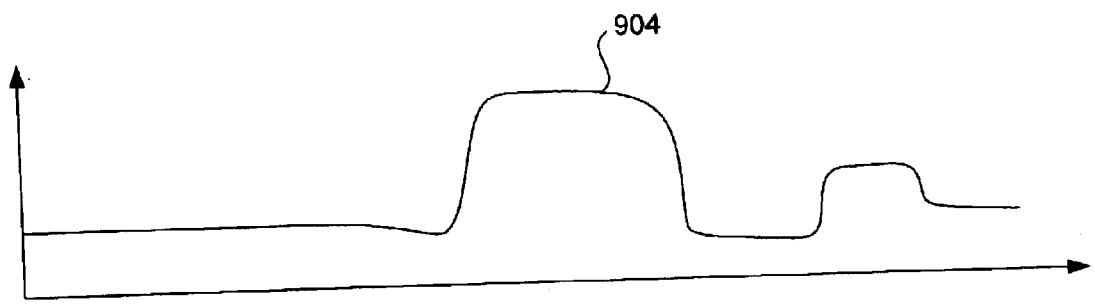

FIG. 9(b) is a depiction of a calculated noise curve 904 associated with the surface measurements 901. The calculated noise curve 904 can be generated using any of a variety of techniques known to those having ordinary skill in the art. Some suitable examples of such methods have been discussed hereinabove.

Figure 9C:
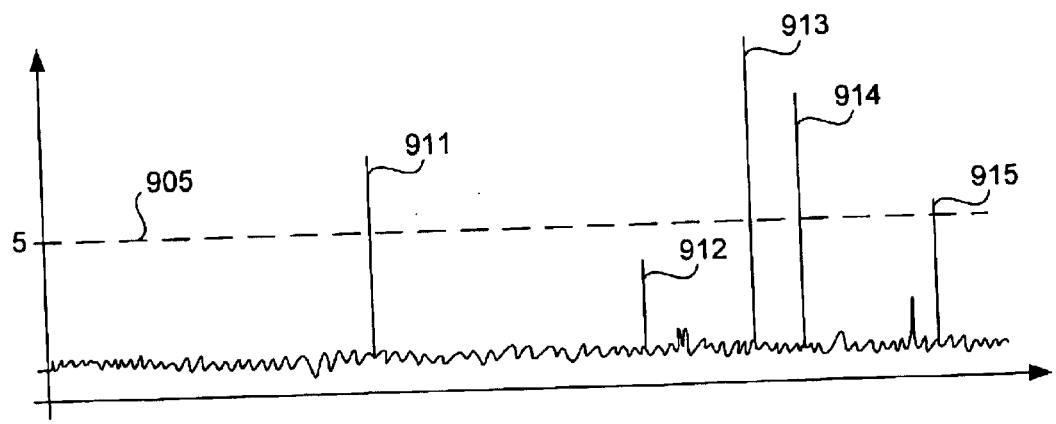

FIG. 9(c) is a signal-to-noise map associated with the inspection surface. The signal amplitudes for each surface measurement (the difference between the detected signal level of the surface measurement and the baseline value associated with that surface measurement) is compared with the background noise (e.g., the calculated noise value) associated with that surface measurement. For example, signal amplitude can be divided by the background noise (e.g., the calculated noise value) to generate a signal-to-noise ratio (SNR). FIG. 9(c) depicts a signal-to-noise map corresponding to the inspection surface mapped to FIGS. 9(a) and 9(b). For most surface measurements the SNR is near 1. However, when the surface measurements vary much from the background noise (e.g., the calculated noise curve) the SNR increases. This embodiment can readily identify defects in both quiescent regions and noisy regions of an inspection surface without any significant changes to the physical instrumentation making the measurements.

Using such a method, a SNR threshold can be used to identify defects. In one embodiment, depicted in FIG. 9(c), the SNR threshold 905 is set at a SNR of 5. If the SNR associated with a surface measurement exceeds the SNR threshold 905, the surface measurement can be identified as a defect. In the depicted embodiment, surface measurements 911, 913, 914, and 915 all have SNR's in excess of 5 and are therefore classified as defects. In contrast, surface measurement 912 has a SNR of less than 5 and is not classified as a defect under the existing threshold 905. Depending on the needs of the process engineer, the SNR threshold can be adjusted to identify defects at higher or lower SNR's. Moreover, the use of SNR introduces an element of confidence in the identification of defects. For example, defects having SNR's of greater than 10 can be identified as defects with an extremely high degree of confidence. Correspondingly, defects having SNR's of in the range of about 5 to 10 can be identified as defects with a fairly high degree of confidence. Also, if desired defects can be identified as having SNR's of in the range of about 3–5. Not surprisingly, the level of confidence in such defects will be rather less than that for those defects identified at higher SNR's. Of course, other threshold values can and should be used depending on the needs of the various quality control and/or inspection methods and individuals. This enables the methods of the present invention to adapt to a wide range of confidence levels as may be necessary to accommodate customer needs. This type of information can be very valuable to those involved in or related to semiconductor fabrication. One extremely advantageous feature of this invention is that the SNR itself adapts to the surface noise. Thus, in order to be a defect in a noisy region, a defect must be more substantial to produce a given SNR. Whereas, in a more quiescent region a smaller defect can produce the same SNR because the background noise is lower. Thus, by using SNR methodologies in accordance with the principles of the present invention defects can be identified consistently on surfaces with varying surface properties. Moreover, SNR methodologies of the present invention enable such defects to be reported with a high degree of confidence and with a reduced incidence of false positives.

Additionally, rather than present the information in a linear two-axis mapping of the inspection surface, the information can be presented in other formats. The inventors specifically contemplate that defect information (e.g., SNR) can be presented in a more representational top down view corresponding to the actual inspection surface. Alternatively, three-axis views of the inspection surface that include more information can also be presented. It should be understood that these embodiments are only examples and, as is known to those having ordinary skill in the art, many other implementations of the basic principles of the invention can be used in the embodiments of the present invention.

Figure 10:
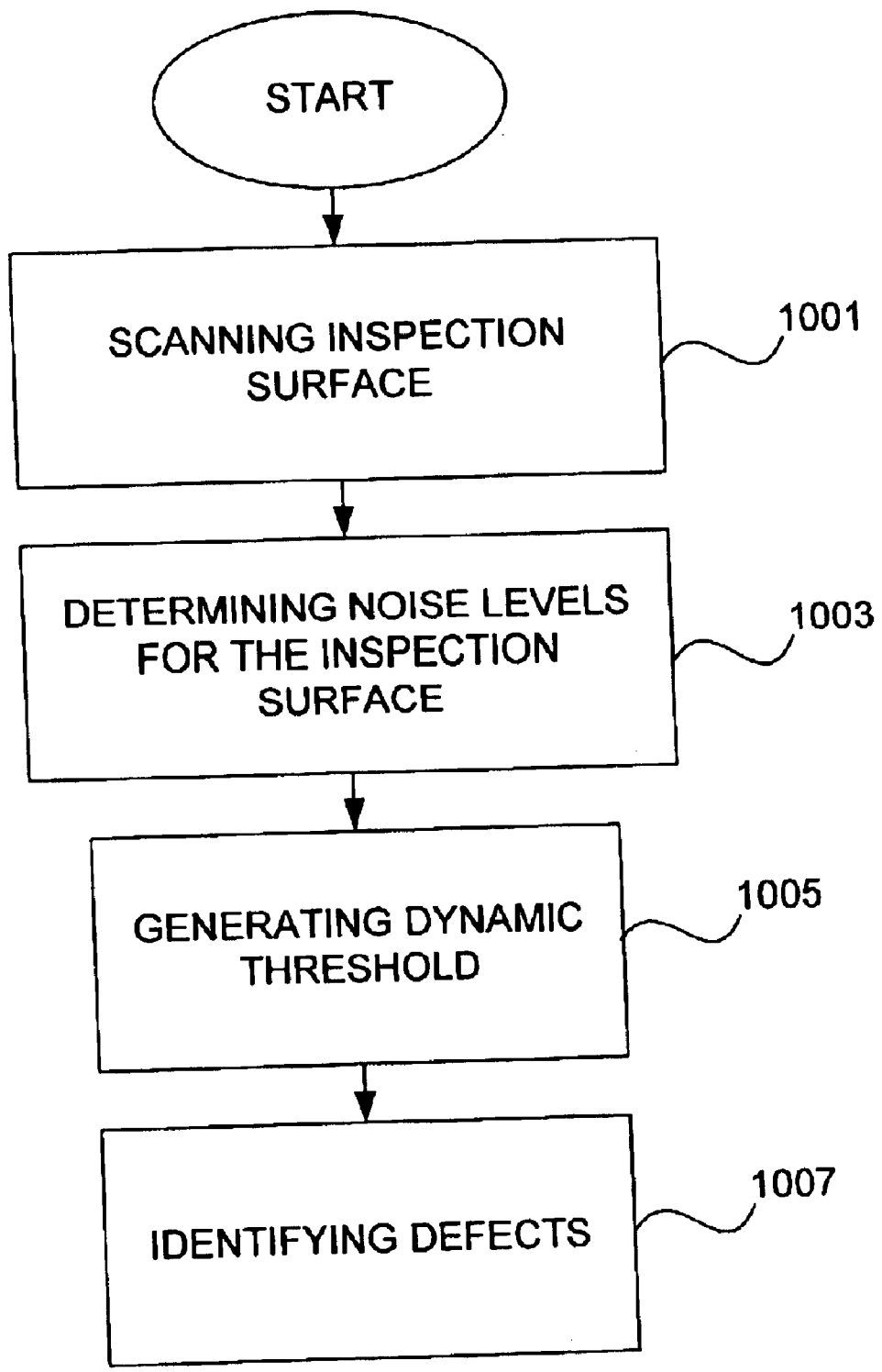
FIG. 10 is a flow diagram illustrating one embodiment of a process for inspecting a surface of an inspection surface in accordance with the principles of the present invention.

FIG. 10 is a flow diagram illustrating one embodiment of a process for inspecting a surface of an inspection surface in accordance with the principles of the present invention. Such a surface inspection method comprises scanning an inspection surface to obtain surface measurements (Step 1001). Suitable scanning approaches are discussed hereinabove. The surface measurements are used to determine noise levels characteristic of the inspection surface (Step 1003). Suitable methods for determining noise levels in an inspection surface are discussed hereinabove. The noise levels are used to generate a dynamic threshold that adapts to the noise levels in the inspection surface (Step 1005). Suitable methods for generating a dynamic threshold are discussed hereinabove. In-one particular application, the dynamic threshold defines the inspection surface in regimes of varying sensitivity. In another approach, signal-to-noise ratios can be used to set a dynamic threshold for defect detection. Defects are identified by comparing surface measurements with the dynamic threshold (Step 1007). Suitable comparison methods are discussed hereinabove.

The present invention has been particularly shown and described with respect to certain preferred embodiments and specific features thereof. However, it should be noted that the above-described embodiments are intended to describe the principles of the invention, not limit its scope. Therefore, as is readily apparent to those of ordinary skill in the art, various changes and modifications in form and detail may be made without departing from the spirit and scope of the invention as set forth in the appended claims. In particular, it is contemplated by the inventors that a wide range of statistical and signal processing techniques can be used to set suitable dynamic thresholds. Further, reference in the claims to an element in the singular is not intended to mean "one and only one" unless explicitly stated, but rather, "one or more". Furthermore, the embodiments illustratively disclosed herein can be practiced without any element which is not specifically disclosed herein.

We claim:

1. A surface inspection method used for inspecting a substrate, the method comprising:
    scanning an inspection surface to obtain surface measurements;
    determining a baseline associated with the surface measurements by
        filtering the surface measurements to excise surface measurements having high signal intensity values, and
        calculating a baseline using a remaining portion of the surface measurements;
    generating a dynamic threshold associated with the surface measurements; and
    identifying defects based on the comparisons of surface measurements with at least one of the baseline and the dynamic threshold.

2. The surface inspection method of claim 1 wherein identifying defects comprises comparing the surface measurements with the dynamic threshold.

3. The surface inspection method of claim 1 wherein scanning the inspection surface to obtain surface measurements comprises scanning an inspection surface having areas with differing surface characteristics.

4. The surface inspection method of claim 3 wherein inspection surface having areas with differing surface characteristics comprises an inspection surface having areas of varying surface roughness.

5. The surface inspection method of claim 3 wherein inspection surface having areas with differing surface characteristics comprises an inspection surface having areas of varying surface reflectivity.

6. The surface inspection method of claim 3 wherein inspection surface having areas with differing surface characteristics comprises an inspection surface having a patterned surface formed thereon.

7. The surface inspection method of claim 1 including the further step of generating a haze map associated with the inspection surface using the surface measurements.

8. The surface inspection method of claim 7 wherein generating the haze map associated with the inspection surface comprises mapping a received signal corresponding to the surface measurements and mapping at least one of a position and a time corresponding to the obtained surface measurements.

9. The surface inspection method of claim 1 wherein filtering the surface measurements comprises generating a moving average value of signal intensity for the obtained surface measurements, thereby determining the baseline associated with the surface measurements.

10. The surface inspection method of claim 1 wherein filtering the surface measurements comprises generating a moving median value of signal intensity for the obtained surface measurements, thereby determining the baseline associated with the surface measurements.

11. The surface inspection method of claim 1 wherein filtering the surface measurements comprises filtering out measurements of a first group of obtained surface measurements having measurement values in excess of a predetermined first limit and filtering out measurements of a second group of obtained surface measurements having measurement values of less than a predetermined second limit and generating one of a moving average or moving median of a group of remaining surface measurement values thereby determining the baseline associated with the surface measurements.

12. The surface inspection method of claim 1 wherein generating the dynamic threshold associated with the surface measurements comprises,
    comparing surface measurements with the baseline to generate noise level amplitudes associated with the surface measurements; and
    generating a dynamic threshold using the noise level amplitudes so that different values for the dynamic threshold can be obtained based on variations in the noise level amplitudes.

13. A surface inspection method used for inspecting a substrate, the method comprising:
    scanning an inspection surface to obtain surface measurements,
    determining noise levels associated with the inspection surface using the surface measurements wherein,
        filtering the surface measurements to excise surface measurements having high signal intensity values, and
        calculating a baseline using a remaining portion of the surface measurements;
    determining a signal-to-noise ratio for the surface measurements;
    comparing the signal-to-noise ratios for the surface measurements with a signal-to-noise ratio threshold value; and
    identifying potential defects based on the comparisons of the signal-to-noise ratio of the surface measurements with the signal-to-noise threshold value.

14. The surface inspection method of claim 13 wherein generating the baseline is accomplished by filtering the surface measurements to obtain baseline values that change as the properties of the inspection surface change.

15. The surface inspection method of claim 13 wherein determining the signal-to-noise ratio for the surface measurements comprises,
    comparing the surface measurements with the baseline value to generate a signal level amplitude associated with the surface measurements, and
    comparing the signal level amplitude of a surface measurement with the noise amplitude for the surface measurements thereby generating a signal-to-noise ratio value for the surface measurements.

16. The surface inspection method of claim 13 wherein identifying defects comprises identifying individual surface measurements that have signal-to-noise ratio that are greater than those of the signal-to-noise ratio threshold as defects.

17. The surface inspection method of claim 13 wherein identifying defects further includes determining a level of confidence in the defect identification by comparing the signal-to-noise ratio for surface measurement identified as a defect with the signal-to-noise ratio threshold.

18. A surface inspection method used for inspecting a substrate, the method comprising:
   scanning an inspection surface to obtain surface measurements;
   determining a baseline associated with the surface measurements by:
      filtering out measurements of a first group of obtained surface measurements having measurement values in excess of a predetermined first limit;
      filtering out measurements of a second group of obtained surface measurements having measurement values of less than a predetermined second limit; and
      generating one of a moving average or moving median of a group of remaining surface measurement values to determine the baseline associated with the surface measurements;
   generating a dynamic threshold associated with the surface measurements; and
   identifying defects based on the comparisons of surface measurements with at least one of the baseline and the dynamic threshold.

19. The surface inspection method of claim 18 wherein identifying defects comprises comparing the surface measurements with the dynamic threshold.

20. The surface inspection method of claim 18 wherein scanning the inspection surface to obtain surface measurements comprises scanning an inspection surface having areas with differing surface characteristics.

21. The surface inspection method of claim 20 wherein inspection surface having areas with differing surface characteristics comprises an inspection surface having areas of varying surface roughness.

22. The surface inspection method of claim 20 wherein inspection surface having areas with differing surface characteristics comprises an inspection surface having areas of varying surface reflectivity.

23. The surface inspection method of claim 20 wherein inspection surface having areas with differing surface characteristics comprises an inspection surface having a patterned surface formed thereon.

24. The surface inspection method of claim 23 wherein the patterned inspection surface comprises a patterned surface of a semiconductor wafer.

25. A surface inspection method used for inspecting a substrate, the method comprising:
   scanning an inspection surface to obtain surface measurements;
   determining a background noise level in the inspection surface associated with the surface measurements by:
      filtering the surface measurements to excise surface measurements having high signal intensity values, and
      creating a noise map of the inspection surface using a remaining portion of the surface measurements.

* * * * *